(12) United States Patent
McDonald et al.

(10) Patent No.: US 11,026,823 B2
(45) Date of Patent: *Jun. 8, 2021

(54) METHOD AND APPARATUS FOR CONTROLLING THE DEPLOYMENT OF A STENT

(71) Applicant: Vascutek Limited, Strathclyde (GB)

(72) Inventors: Gary Peter McDonald, Glasgow (GB); David Granville Stevenson, Bridge of Weir (GB)

(73) Assignee: Vascutek Limited, Renfrewshire (GB)

( * ) Notice: Subject to any disclaimer, the term of this patent is extended or adjusted under 35 U.S.C. 154(b) by 227 days.

This patent is subject to a terminal disclaimer.

(21) Appl. No.: 16/180,804

(22) Filed: Nov. 5, 2018

(65) Prior Publication Data
US 2019/0070031 A1 Mar. 7, 2019

Related U.S. Application Data

(63) Continuation of application No. 14/123,650, filed as application No. PCT/GB2012/051235 on Jun. 1, 2012, now Pat. No. 10,137,021.

(30) Foreign Application Priority Data

Jun. 3, 2011 (GB) ..................... 1109305

(51) Int. Cl.
*A61F 2/966* (2013.01)
*A61F 2/07* (2013.01)
*A61F 2/95* (2013.01)

(52) U.S. Cl.
CPC ............... *A61F 2/966* (2013.01); *A61F 2/07* (2013.01); *A61F 2/9517* (2020.05); *A61F 2002/9511* (2013.01); *A61F 2002/9665* (2013.01)

(58) Field of Classification Search
CPC ...... A61F 2/966; A61F 2/9661; A61F 2/9517; A61F 2/2439; A61F 2002/9665;
(Continued)

(56) References Cited

U.S. PATENT DOCUMENTS 5,720,776 A 2/1998 Chuter et al.
5,843,162 A 12/1998 Inoue
(Continued)

FOREIGN PATENT DOCUMENTS

EP 0686379 12/1995
EP 0910309 4/1999
(Continued)

OTHER PUBLICATIONS

Office Action for European Application No. 12731617.2 dated Mar. 24, 2016.
(Continued)

*Primary Examiner* — Katherine H Schwiker
(74) *Attorney, Agent, or Firm* — Heslin Rothenberg Farley & Mesiti P.C.; Kristian E. Ziegler, Esq.; John W. Bogers, Esq.

(57) ABSTRACT

A control system for deploying a stent graft including a resilient ring stent at one end, provides a delivery shaft carrying the stent graft with the ring stent adjacent a proximal end of the shaft for insertion into a lumen; a retractable sleeve for containing the stent graft on the delivery shaft; a control handle adjacent the distal end, of the delivery shaft; and stent peak and valley control wires extending from the proximal end of the delivery shaft to peak and valley controllers at the control handle. Use of the control wires effects movement and/or rotation of the graft allowing fine control of deployment in the lumen.

49 Claims, 9 Drawing Sheets

(58) Field of Classification Search
CPC ...... A61F 2002/9511; A61F 2/95; A61F 2/07; A61F 2/954; A61F 2/962; A61F 2/2427; A61F 2/2436; A61F 2002/9505; A61F 2002/9534

See application file for complete search history.

(56) References Cited

U.S. PATENT DOCUMENTS

| | | |
|---|---|---|
| 6,203,568 B1 | 3/2001 | Lombardi et al. |
| 6,278,079 B1 | 8/2001 | McIntyre et al. |
| 6,364,901 B1 | 4/2002 | Inoue |
| 6,635,080 B1 | 10/2003 | Lauterjung et al. |
| 2002/0151953 A1 | 10/2002 | Chobotov et al. |
| 2003/0233140 A1 | 12/2003 | Hartley et al. |
| 2004/0199245 A1 | 10/2004 | Lauterjung |
| 2008/0132989 A1 | 6/2008 | Snow et al. |
| 2009/0030497 A1 | 1/2009 | Metcalf et al. |
| 2009/0082845 A1 | 3/2009 | Chobotov |
| 2009/0099640 A1 | 4/2009 | Weng |
| 2009/0099650 A1 | 4/2009 | Bolduc et al. |
| 2009/0182405 A1 | 7/2009 | Arnault De La Menardiere et al. |
| 2010/0076541 A1 | 3/2010 | Kumoyama |
| 2011/0054585 A1 | 3/2011 | Osborne |

FOREIGN PATENT DOCUMENTS

| | | |
|---|---|---|
| EP | 1302178 | 10/2002 |
| EP | 2143404 | 1/2010 |
| EP | 1796589 | 8/2010 |
| GB | 2474252 | 10/2009 |
| WO | 9737617 | 10/1997 |
| WO | 03101518 | 12/2003 |
| WO | 2006034340 | 3/2006 |
| WO | 2008098255 | 8/2008 |
| WO | 2011056797 | 5/2011 |

OTHER PUBLICATIONS

International Search Report from PCT/GB2012/051235 dated Aug. 21, 2012.
United Kingdom Intellectual Property Office Search Report for GB1209760.6 dated Oct. 2, 2012.
Parodi et al., Annals of Vascular Surgery (1991) 5:491-499.

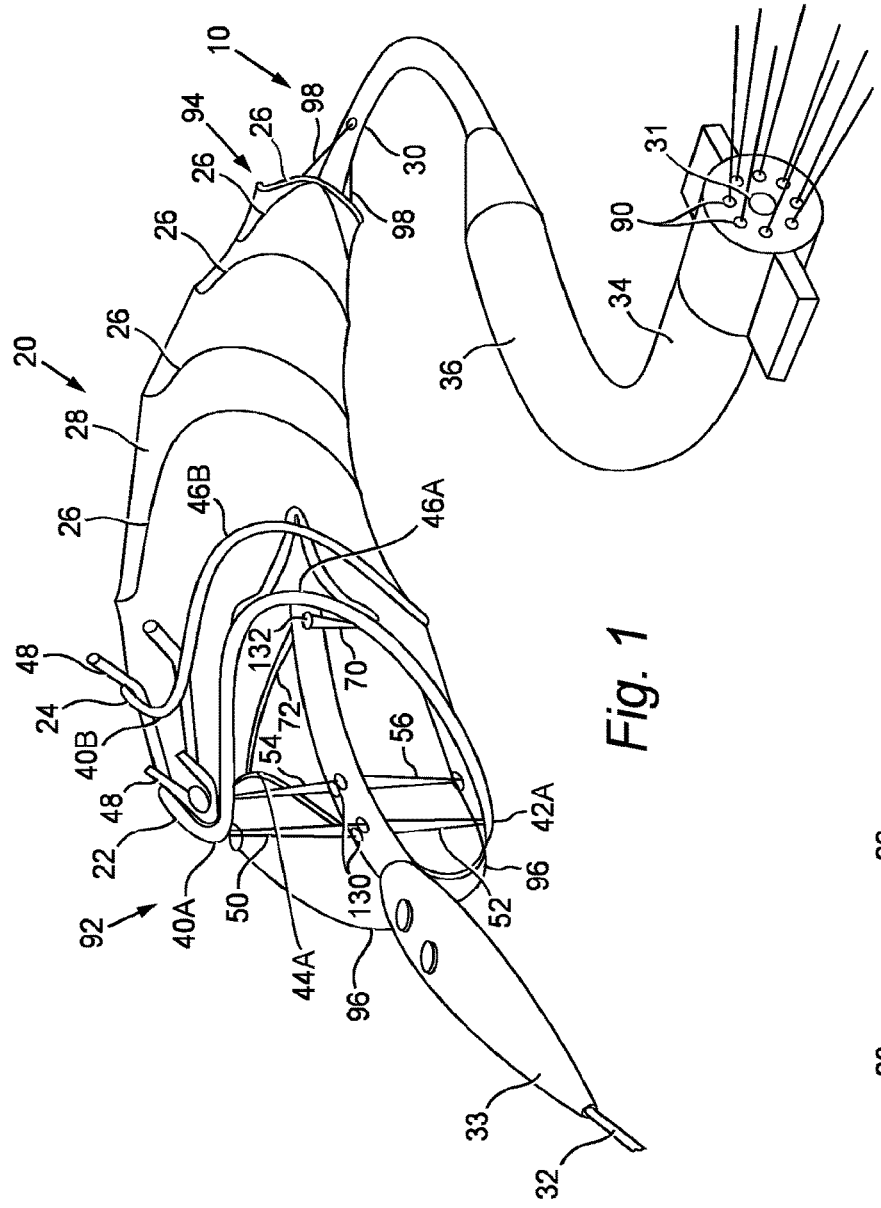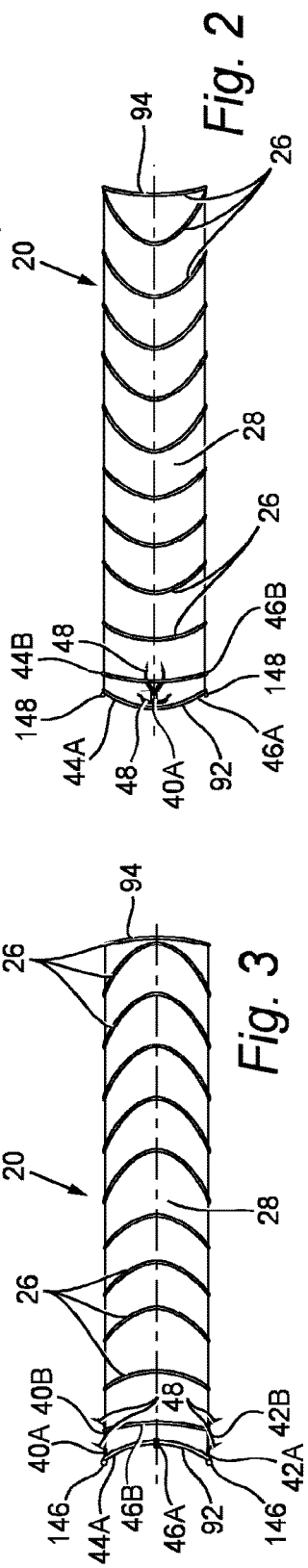

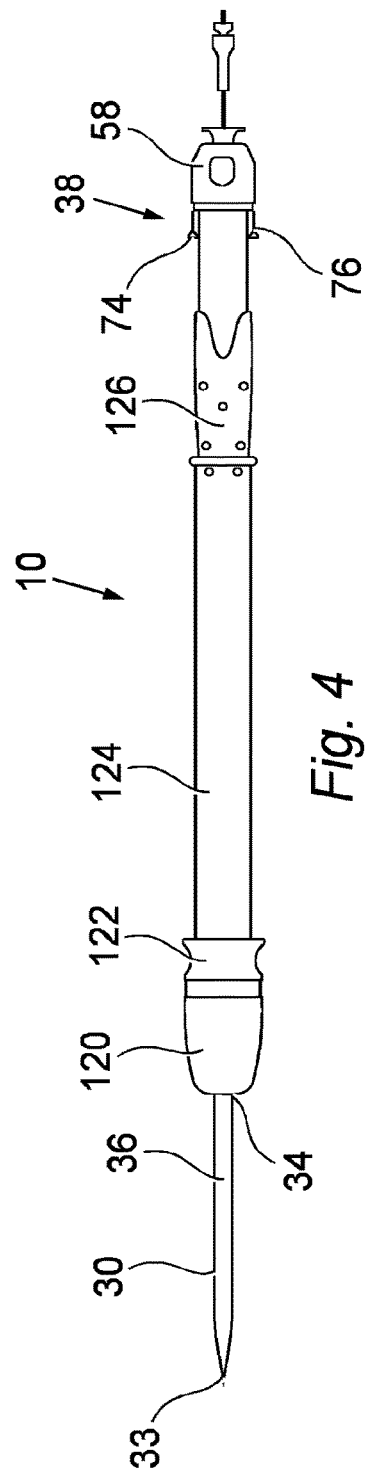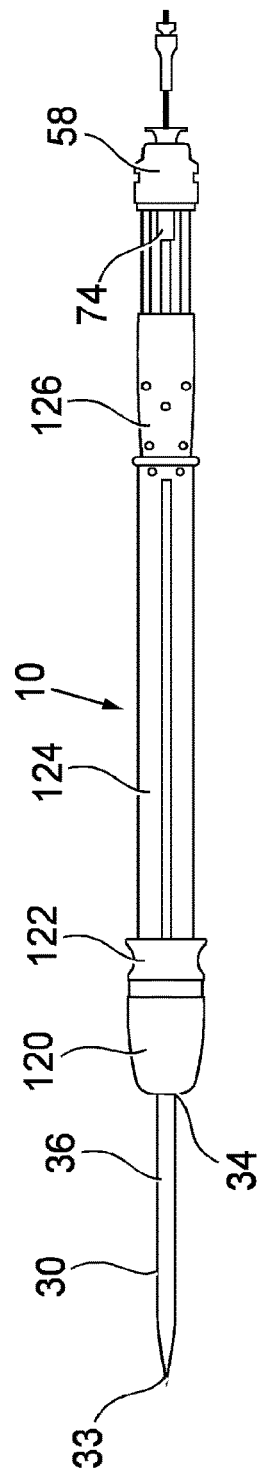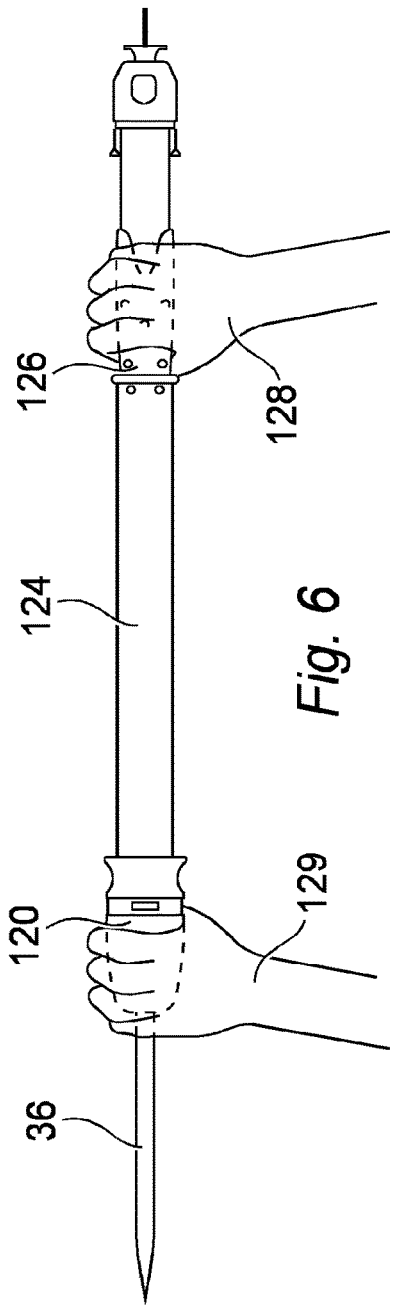

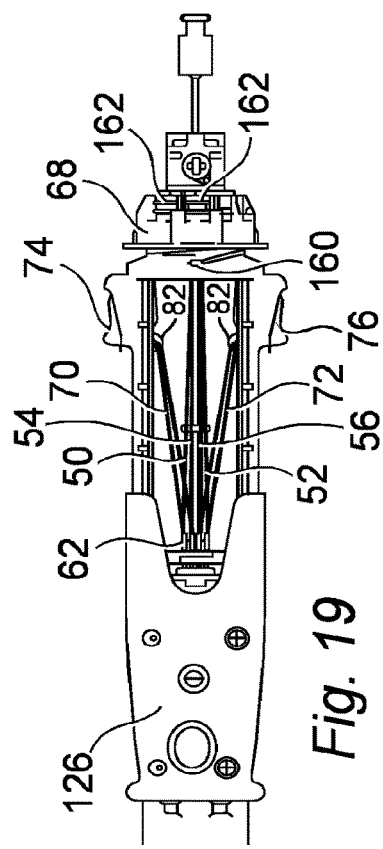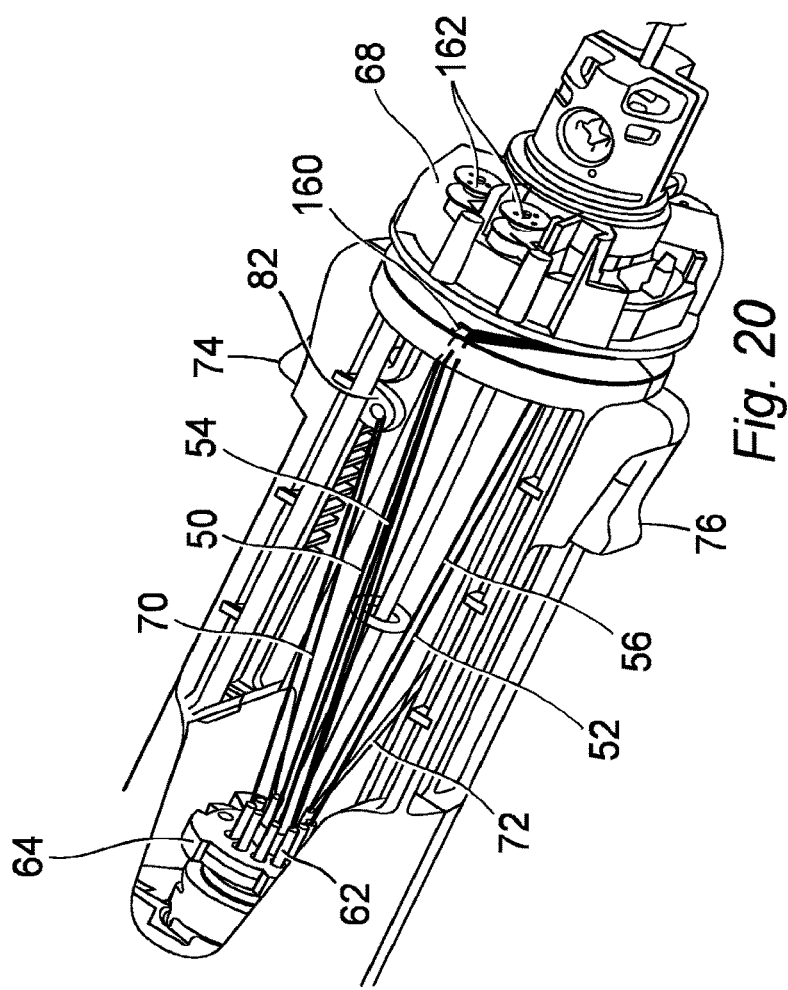

METHOD AND APPARATUS FOR CONTROLLING THE DEPLOYMENT OF A STENT

CROSS-REFERENCE TO RELATED APPLICATIONS

This application is a continuation of U.S. non-provisional application Ser. No. 14/123,650, filed Dec. 3, 2013, entitled METHOD AND APPARATUS FOR CONTROLLING THE DEPLOYMENT OF A STENT, which is a U.S. national stage application of PCT international patent application No. PCT/GB2012/051235, filed Jun. 1, 2012, entitled METHOD AND APPARATUS FOR CONTROLLING THE DEPLOYMENT OF A STENT, which claims the benefit of United Kingdom patent application No. 1109305.1, filed Jun. 3, 2011, entitled METHOD AND APPARATUS FOR CONTROLLING THE DEPLOYMENT OF A STENT, which are hereby incorporated herein by reference in their entireties.

FIELD OF THE INVENTION

The present invention relates to the deployment of a stent element, and in particular to the deployment of a stent element to stabilise a tubular prosthesis.

BACKGROUND TO THE INVENTION

Artificial prostheses consisting of a tubular conduit having an open lumen are well-known and are used in medicine to replace diseased or damaged natural body lumens, such as, for example, blood vessels or other hollow organs for example bile ducts, sections of intestine or the like. The most common use of such artificial prostheses is to replace diseased or damaged blood vessels.

A number of vascular disorders can be treated by use of an artificial prosthesis. One relatively common vascular disorder is an aneurysm. Aneurysm occurs when a section of natural blood vessel wall, typically of the aortic artery, dilates and balloons outwardly. Whilst small aneurysms cause little or no symptoms, larger aneurysms pose significant danger to a patient. Rupture of an aortic aneurysm can occur without warning and is usually fatal, so significant emphasis is placed on early diagnosis and treatment. With an increasing ageing population, the incidence of aneurysm continues to rise in western societies.

Provided that an aneurysm is diagnosed prior to rupture, surgical treatment to repair the affected vessel wall is effective. Surgical treatment of aneurysm involves the replacement or reinforcement of the aneurismal section of aorta with a synthetic graft or prosthesis under general anaesthesia allowing the patient's abdomen or thorax to be opened (see Parodi et al., Annals of Vascular Surgery (1991) 5:491-499). The patient will then have a normal life expectancy.

Surgical repair of aneurysm is however a major and invasive undertaking and there has been much effort in developing less invasive methods. Currently, aneurysm repair generally involves the delivery by catheter of a fabric or ePTFE graft which is retained at the required location by deployment of metallic stent elements. The ability to deliver the graft/stent device by catheter reduces the surgical intervention to a small cut-down to expose the femoral artery and, in suitable circumstances, the device can be deployed percutaneously. Catheter delivery is beneficial since the reduced invasive nature of the procedure allows utilisation of a local anaesthetic and leads to reduced mortality and morbidity, as well as decreased recovery time. For example, endovascular repair is typically used for repair of infra-renal abdominal aortic aneurysms where the graft is placed below the renal arteries. Many different types of devices useful for endovascular repair are now available, for example a resiliently engaging endovascular element described in U.S. Pat. No. 6,635,080 (Vascutek) or a tubular fabric liner having a radially expandable supporting frame and a radiopaque marker element stitched to the liner as disclosed in U.S. Pat. No. 6,203,568 (Medtronic).

However, whilst the endovascular repair of aneurysms is now accepted as the method of choice, the technique has significant limitations and is not suitable for all patients.

As mentioned above, other vascular disorders are treatable by use of a vascular prosthesis. Examples include (but not limited to) occlusions, stenosis, vascular damage due to accident or trauma, and the like. Vascular prostheses are also used in by-pass techniques.

Endovascular techniques involve the delivery of a prosthesis by catheter. Since the internal lumen of the catheter defines the maximum dimensions of the prosthesis to be inserted, much effort has been expended in the design of prostheses which can be packaged in a minimal volume, and are easy to deploy once positioned at the required location.

One successful type of prosthesis is a stent graft comprising a conduit formed of a flexible sleeve attached to a rigid support or stent. The sleeve will typically be made of a fabric (usually a knitted or woven fabric) of ePTFE, PTFE, polyester (for example DACRON), polyethylene or polypropylene and may optionally be coated to reduce friction; discourage clotting or to deliver a pharmaceutical agent. The fabric will generally be porous on at least one surface to enable cell ingrowth.

The stent may be self-expandable and formed of a shape memory material, such as nitinol (a nickel-titanium alloy).

The stent grafts are inserted using a delivery catheter and, once correctly located at the site requiring treatment, are deployed by the withdrawal of a delivery sheath of the delivery catheter. The self-expandable stents are deployed by expanding radially upon release from the delivery sheath. Once deployed, the stents hold the graft in location by contact with the inner wall of the blood vessel.

One suitable stent design is a series of ring stent elements formed from discrete rings of a shape memory material, such as nitinol, attached to the fabric sleeve at spaced intervals. Such a design fulfils the requirements for minimal volume when packaged and, once delivered, readily expands to maintain the patency of the fabric lumen. However, stent grafts having such ring stent elements have the disadvantage that the rings are not readily capable of being contracted again and so do not allow adjustment of the position of the stent graft once deployed.

It is an object of the present invention to over come one or more of the aforementioned problems.

SUMMARY OF THE INVENTION

According to a first aspect of the present invention there is provided a delivery apparatus for controlling the deployment of a stent, the apparatus comprising:
  a delivery shaft adapted to carry a tubular prosthesis thereon and having a proximal end for insertion into a lumen and a distal end remote from the proximal end;
  a retractable sleeve adapted to contain a tubular prosthesis carried on the delivery shaft;
  a control handle adjacent the distal end of the delivery shaft;

at least one stent peak control wire extending from the proximal end of the delivery shaft to the control handle;

a peak controller at the control handle adapted to control the position of the stent peak control wire.

The term "wire" as used in this specification includes metallic and non-metallic wire, thread and filament.

The apparatus may comprise two or more stent peak control wires extending from the proximal end of the delivery shaft to the control handle, and the peak controller may be adapted to control the position of the two or more stent peak control wires.

The apparatus may further comprise:

at least one stent valley control wire extending from the proximal end of the delivery shaft to the control handle; and a valley controller at the control handle adapted to control the position of the stent valley control wire.

The apparatus may comprise two stent valley control wires extending from the proximal end of the delivery shaft to the control handle, and the apparatus may include two valley controllers at the control handle, each valley controller being adapted to control the position of a respective stent valley control wire.

The delivery shaft may include a plurality of longitudinal passages, each control wire extending through a respective longitudinal passage.

The apparatus may include one or more tow wires provided at the proximal end of the delivery shaft adapted for connection to a proximal end of a tubular prosthesis carried on the delivery shaft. The apparatus may include one or more back tether wires provided between the proximal end of the delivery shaft and the control handle adapted for connection to a distal end of a tubular prosthesis carried on the delivery shaft.

The control handle may include a manifold having a plurality of apertures, each control wire extending through a respective aperture. The manifold may include a plurality of haemostasis valves switchable between open and closed positions.

The peak controller may comprise a rotatable collar. The rotatable collar may be mounted for rotation about a longitudinal axis of the control handle. The peak controller may include a winder which rotates with the collar and on which are wound the stent peak control wires.

Each valley controller may comprise a slider. Each valley controller may include an actuating surface and a ratchet adapted to allow the slider to move when the actuating surface is depressed and to hold the slider in an engaged position when the actuating surface is released. The sliders may be mounted for longitudinal sliding movement. Each slider may include a wire connector to which is connected the respective stent valley control wire.

Preferably the delivery shaft includes a plurality of peak apertures adjacent the proximal end thereof, each stent peak control wire extending through one of said plurality of peak apertures. Preferably the delivery shaft includes a plurality of valley apertures adjacent the proximal end thereof, each stent valley control wire extending through one of said plurality of valley apertures. Preferably the valley apertures are arranged between the peak apertures and the distal end.

The control wires may be looped wires which extend from the control handle to the proximal end of the delivery shaft and back to the control handle.

The apparatus may include a plurality of release wires extending from the control handle along the delivery shaft and having a proximal end at or near the proximal end of the delivery shaft and a distal end at the control handle. The proximal end of each release wire is adapted to be connected to a respective connection between a tubular prosthesis carried on the delivery shaft and one of the stent peak control wires, the stent valley control wires, the tow wires and the back tether wires. The distal end of each release wire may be connected to a release clip mounted on the control handle. The release clip may be removed from the control handle and pulled with its corresponding release wire or wires away from the apparatus, thereby releasing the respective connection between a tubular prosthesis carried on the delivery shaft and one of the stent peak control wires, the stent valley control wires, the tow wires and the back tether wires.

According to a second aspect of the present invention there is provided a method of deploying a ring stent, the method comprising the steps of:

providing a tubular prosthesis including a ring stent thereon on a delivery shaft, the delivery shaft having a proximal end for insertion into a lumen and a distal end remote from the proximal end, and having two stent peak control wires extending from the proximal end to the distal end;

attaching the first ends of two stent peak control wires to first and second diametrically opposed peak connection points on the tubular prosthesis adjacent the ring stent;

attaching the second ends of the two stent peak control wires to a peak controller provided at a control handle adjacent the distal end of the delivery shaft;

holding the two stent peak control wires under tension such that the peak connection points are held by the stent peak control wires in a folded arrangement towards the delivery shaft; and operating the peak controller to permit movement of the stent peak control wires along the delivery shaft such that the peak connection points are urged by the resilience of the ring stent to move away from the delivery shaft and the ring stent adopts a partially deployed position.

The peak connection points may be on the ring stent.

The delivery shaft may include two stent valley control wires extending from the proximal end to the distal end, and the method may comprise the further steps of:

attaching the first ends of the two stent valley control wires to first and second diametrically opposed valley connection points on the tubular prosthesis adjacent the ring stent, the valley connection points being provided midway between the peak connection points;

attaching the second ends of the two stent valley control wires to first and second valley controllers respectively provided at the control handle;

holding the two valley peak control wires under tension such that the valley connection points are held by the stent valley control wires in a folded arrangement towards the delivery shaft; and selectively operating one of the first and second valley controllers to permit movement of the stent valley control wires along the delivery shaft such that the first or second valley connection point is urged by the resilience of the ring stent to move away from the delivery shaft and the ring stent is rotated in the partially deployed position.

The valley connection points may be on the ring stent or may be on a valley line between two adjacent ring stents on the tubular prosthesis.

The method may include the further step of selectively operating the other of the first and second valley controllers to permit movement of the stent valley control wires along the delivery shaft such that both the first and second valley connection points are urged by the resilience of the ring stent to move away from the delivery shaft and the ring stent adopts a fully deployed position.

The method may include the further step of selectively operating one or more of the peak controller and first and second valley controllers to pull at least some of the control wires along the delivery shaft such that one or more of the connection points adjacent the ring stent are moved towards the delivery shaft against the resilience of the ring stent to permit the ring stent to be moved in position.

The control wires may be looped wires which extend from the control handle to the peak or valley connection points and back to the control handle. The peak or valley connection points may be eyelets through which the looped wires are threaded.

The step of operating the peak controller may include rotating a rotatable collar to wind or unwind the stent peak control wires on a winder.

The step of operating the first or second valley controller may include moving a slider which includes a wire connector to which is connected the respective stent valley control wire.

According to a third aspect of the present invention there is provided a method of causing the rotation of a ring stent in a lumen, the method comprising the steps of:
  providing a tubular prosthesis including a ring stent thereon on a delivery shaft, the delivery shaft having a proximal end for insertion into a lumen and a distal end remote from the proximal end, and having two stent valley control wires extending from the proximal end to the distal end;
  attaching the first ends of two stent valley control wires to first and second diametrically opposed valley connection points on the tubular prosthesis adjacent the ring stent;
  attaching the second ends of the two stent valley control wires to first and second valley controllers respectively provided at a control handle adjacent the distal end of the delivery shaft;
  holding the two stent valley control wires under tension such that the valley connection points are held by the stent valley control wires in a folded arrangement towards the delivery shaft; and
  selectively operating one of the first and second valley controllers to permit movement of the stent valley control wires along the delivery shaft such that the first or second valley connection point is urged by the resilience of the ring stent to move away from the delivery shaft and the ring stent is rotated.

The valley connection points may be on the ring stent or may be on a valley line between two adjacent ring stents on the tubular prosthesis.

The method may include the further step of selectively operating the other of the first and second valley controllers to permit movement of the stent valley control wires along the delivery shaft such that both the first and second valley connection points are urged by the resilience of the ring stent to move away from the delivery shaft by a respective selected amount and the ring stent adopts a selected rotational position.

The delivery shaft may include two stent peak control wires extending from the proximal end to the distal end, and the method may comprise the further steps of:
  attaching the first ends of the two stent peak control wires to first and second diametrically opposed peak connection points on the tubular prosthesis adjacent the ring stent, the peak connection points being provided midway between the valley connection points;
  attaching the second ends of the two stent peak control wires to a peak controller provided at a control handle adjacent the distal end of the delivery shaft;
  holding the two stent peak control wires under tension such that the peak connection points are held by the stent peak control wires in a folded arrangement towards the delivery shaft; and
  operating the peak controller to permit movement of the stent peak control wires along the delivery shaft such that the peak connection points are urged by the resilience of the ring stent to move away from the delivery shaft and the ring stent adopts a fully deployed position.

The peak connection points may be on the ring stent.

The method may include the further step of selectively operating one or more of the peak controller and first and second valley controllers to pull at least some of the control wires along the delivery shaft such that one or more of the connection points adjacent the ring stent are moved towards the delivery shaft against the resilience of the ring stent to permit the ring stent to be moved in position.

The control wires may be looped wires which extend from the control handle to the peak or valley connection points and back to the control handle. The peak or valley connection points may be eyelets through which the looped wires are threaded.

The step of operating the peak controller may include rotating a rotatable collar to wind or unwind the stent peak control wires on a winder.

The step of operating the first or second valley controller may include moving a slider which includes a wire connector to which is connected the respective stent valley control wire.

According to a fourth aspect of the present invention there is provided a stent system comprising a tubular prosthesis including a resilient ring stent at a first end thereof, and an apparatus for controlling the deployment of the ring stent, the apparatus comprising:
  a delivery shaft carrying the tubular prosthesis thereon and having a proximal end for insertion into a lumen and a distal end remote from the proximal end, the ring stent being adjacent the proximal end;
  a retractable sleeve adapted to contain the tubular prosthesis carried on the delivery shaft;
  a control handle adjacent the distal end of the delivery shaft;
  a first stent peak control wire extending from the proximal end of the delivery shaft to the control handle; and
  a peak controller at the control handle adapted to control the position of the first stent peak control wire;
  wherein the stent peak control wire is connected to a first peak connection point on the tubular prosthesis adjacent the ring stent.

The apparatus may further include a second stent peak control wire extending from the proximal end of the delivery shaft to the control handle, wherein the peak controller is adapted to control the position of the second stent peak control wire, and wherein the second stent peak control wire is connected to a second peak connection point on the tubular prosthesis adjacent the ring stent diametrically opposed to the first peak connection point.

The peak connection points may be on the ring stent.

The apparatus may further include a first stent valley control wire extending from the proximal end of the delivery shaft to the control handle, and a first valley controller adapted to control the position of the first stent valley control wire, wherein the first stent valley control wire is connected to a first valley connection point on the tubular prosthesis adjacent the ring stent interposed between the first and second peak connection points.

The apparatus may further include a second stent valley control wire extending from the proximal end of the delivery shaft to the control handle, and a second valley controller adapted to control the position of the second stent valley control wire, wherein the second stent valley control wire is connected to a second valley connection point on the tubular prosthesis adjacent the ring stent diametrically opposed to the first valley connection point.

The valley connection points may be on the ring stent or may be on a valley line between two adjacent ring stents on the tubular prosthesis.

Preferably the apparatus is an apparatus according to the first aspect of the invention.

The ring stent may have the shape of the perimeter of a saddle. The first and second peak connection points may be provided at peaks of the saddle. The first and second valley connection points may be provided at valleys of the saddle. Preferably the distance between the valley connection points and the control handle is less than the distance between the peak connection points and the control handle.

Preferred or alternative features of each aspect or embodiment of the invention apply mutatis mutandis to each other aspect or embodiment of the invention, unless the context demands otherwise.

DESCRIPTION OF THE DRAWINGS

The present invention will now be further described by reference to the following figures, in which:

FIG. 1 is a schematic illustration of a delivery shaft and stent graft of a delivery apparatus of the invention;

FIGS. 2 and 3 are a top view and a side view respectively of the stent graft of FIG. 1;

FIGS. 4 and 5 are a top view and a side view respectively of the apparatus of FIG. 1;

FIG. 6 is a schematic illustration of an operator operating the apparatus of FIG. 1;

FIG. 19 is a partial top view of the control handle of the delivery apparatus of FIG. 1 with the control wires installed;

FIG. 20 is a partial isometric view of the control handle of the delivery apparatus of FIG. 1 with the control wires installed;

DESCRIPTION OF EMBODIMENTS OF THE INVENTION

Figure 7:
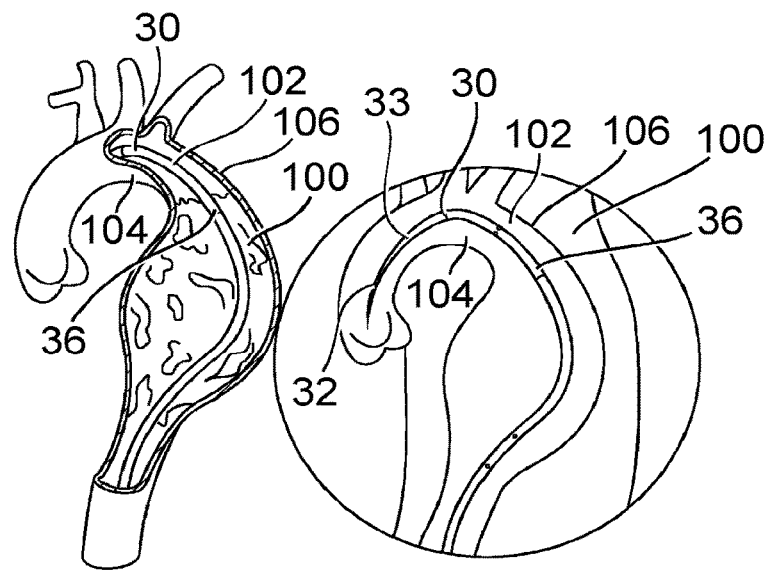
FIG. 7 is a schematic illustration of a thoracic arch during a first stage of a method of deployment of a ring stent according to the invention.

Referring to FIG. 1, there is shown a delivery apparatus 10 used to deliver a tubular prosthesis, for example a stent graft 20, to the thoracic arch. The delivery apparatus 10 includes a delivery shaft 30 having a central passage 31 adapted to travel on a guide wire 32 provided in the thoracic arch, so that the shaft 30 can be extended within the body of a patient to the correct location. Such guide wires are known in the art and are not described further.

The stent graft is shown in more detail in FIGS. 2 and 3. The stent graft includes a first ring stent 22, a second ring stent 24 and a number of other ring stents 26. The ring stents 22, 24, 26 are attached to a sleeve 28 of the stent graft 20. The sleeve 28 is a flexible tubular conduit having the ring stents 22, 24, 26 attached thereto to maintain the patency of the sleeve lumen after deployment. The sleeve 28 is a woven or knitted flexible fabric which is generally impervious to fluid such as blood. Suitable materials include polyester, such as Dacron. The sleeve 28 may be coated to reduce blood clotting, to reduce friction or to deliver a medicament. The stent graft 20 shown in FIGS. 1 to 3 in the expanded or deployed configuration.

The ring stents 22, 24, 26 are typically formed from a resilient alloy material suitable for medical use, such as nitinol, and are generally saddle shaped. The first ring stent 22 has two diametrically opposed ring stent peaks 40A, 42A and two diametrically opposed ring stent valleys 44A, 46A. The ring stent 22 can fold about its peaks 40A, 42A and valleys 44A, 46A to adopt a compact folded configuration, but the resilience of the ring stent urges it towards the expanded position shown in FIGS. 1 to 3. Similarly the second ring stent 24 has two diametrically opposed ring stent peaks 40B, 42B and two diametrically opposed ring stent valleys 44B, 46B, and can fold in the same way about its peaks and valleys. The folding of at least some of the peaks and valleys of the first and second ring stents 22, 24 can be selectively controlled by control wires, as is described below. The remaining stents are also capable of folding about their peaks and valleys so that they can adopt a compact folded configuration when held in a retractable sleeve 36, but their peaks and valleys are not selectively foldable.

Adjacent to the ring stent peaks 40, 42 of the first and second ring stents 22, 24 are provided hooks 48 which engage with the lumen in which the stent graft 20 is deployed when the ring stent peaks 40, 42 expand away from the delivery shaft 30. Also adjacent to the ring stent peaks 40, 42 of the first and second ring stents 22, 24 are provided connection loops 146, which serve as stent peak connection points, and through which stent peak control wires 50, 52, 54, 56 are connected, as described below. Further connection loops 148 are provided adjacent to the ring stent valleys 44, 46 of the first ring stent 22. The loops 148 serve as stent valley connection points for the connection of stent valley control wires 70, 72, as described below. Instead of providing stent valley connection points at the first ring stent 22, as illustrated in FIGS. 1 to 3, they may be provided at the second ring stent 24, or at both the first and second ring stents 22, 24, or at both the first and third ring stents 22, 24, or on the fabric of the sleeve 28 on the valley line between the first and second ring stents 22, 24. The control wires may be of any suitable material and in a preferred embodiment are of Ultra High Molecular Weight Polyethylene.

The delivery apparatus 10 is shown in FIGS. 4 to 6. The delivery apparatus 10 comprises a delivery shaft 30 having a proximal end 33 and a distal end 34. Surrounding the delivery shaft is a retractable sleeve 36 which can be retracted using a retraction wheel 120 or a manual slider 122, which serve to retract the retractable sleeve 36 inside the shaft 124 of the apparatus. The retraction mechanism, including the retraction wheel 120 and manual slider 122, does not form part of the present invention, and is described in more detail in the applicant's UK patent application GB1109316.8 filed 3 Jun. 2011.

At the distal end of the shaft 124 is a grip portion 126, which the operator holds in one hand 128 while operating the retraction wheel 120 with the other hand 129 to retract the sleeve 36. Beyond the grip portion 126 is the control handle 38 which is used to control the deployment and position of the first and/or second ring stents 22, 24. The control handle 38 includes a rotary collar 58 which serves as a peak controller and two sliders 74, 76 which serve as valley controllers.

The use of the delivery apparatus 10 to deploy a ring stent 22 of a stent graft 20 in the thoracic arch 100 will now be described with reference to FIGS. 7 to 13, which show the thorax and apparatus schematically as well as images of the sort produced by a suitable medical imaging device. Although the invention is described with reference to the thoracic arch, it is to be understood that the apparatus and method of the invention may be used in any location in a lumen 100 where control of the angle and position of a ring stent is required, and the invention is not limited to use with the thorax.

A guide wire 32 is located to guide the delivery apparatus 10. An intended landing zone 102 for the ring stent 22 at the end of the stent graft 20 is identified. Preferably the intended landing zone is perpendicular to the vessel wall 104, 106 on both the inner and outer aspects of the thoracic arch. The delivery shaft 30, on which the stent graft 20 is held by the retractable sleeve 36, is slowly advanced along the guide wire 32 until the ring stent 22, which is in its folded state within the retractable sleeve 36, is at the intended landing zone, as shown in FIG. 7.

Figure 8:
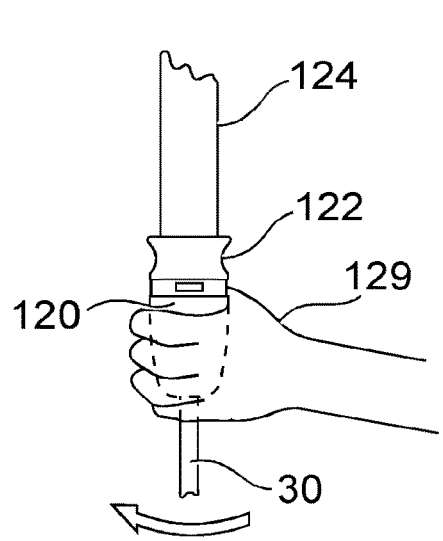
FIG. 8 is a side view of the handle of the delivery apparatus during a second stage of a method of deployment of a ring stent according to the invention.
Figure 9:
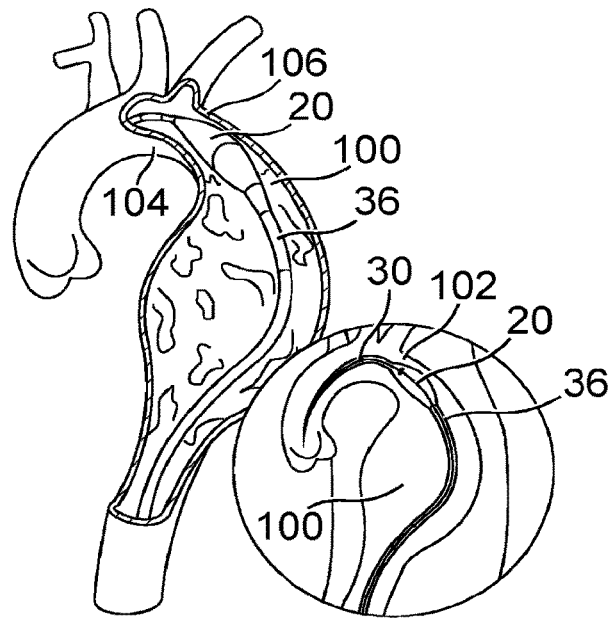
FIG. 9 is a schematic illustration of a thoracic arch during the second stage of a method of deployment of a ring stent according to the invention.
Figure 10:
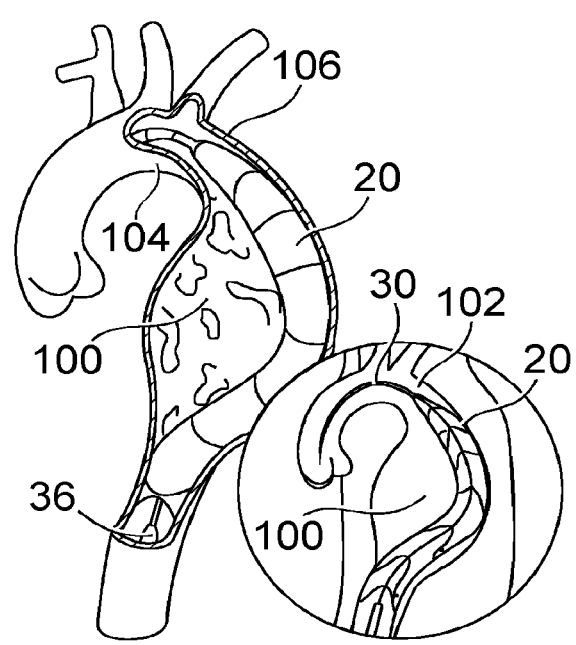
FIG. 10 is a schematic illustration of a thoracic arch during a third stage of a method of deployment of a ring stent according to the invention.

The retraction wheel 120 is then slowly rotated, as shown in FIG. 8, to retract the sleeve 36 to the position shown in FIG. 9. The first ring stent 22 is prevented from unfolding by the stent peak control wires 50, 52 which hold the ring stent peaks 40A, 42A towards the delivery shaft 30. However the ring stents 26 which are not restrained by control wires are free to expand as the sleeve 36 is retracted so that the stent graft 20 adopts a tapered balloon shape. At this stage some longitudinal movement or rotation of the apparatus 10 and delivery shaft 30 is possible to ensure correct orientation and positioning of the ring stent peaks 40, 42 and valleys 44, 46, since the hooks 48 which engage with the internal surface of the lumen 100 must be orientated correctly. Once the required position and orientation have been achieved, the stent graft 20 can be unsheathed from the sleeve 36 more rapidly by sliding the manual slider 122, until the stent graft 20 is fully unsheathed as shown in FIG. 10. The release wire 140 associated with the retractable sleeve can then be removed.

Figure 11:
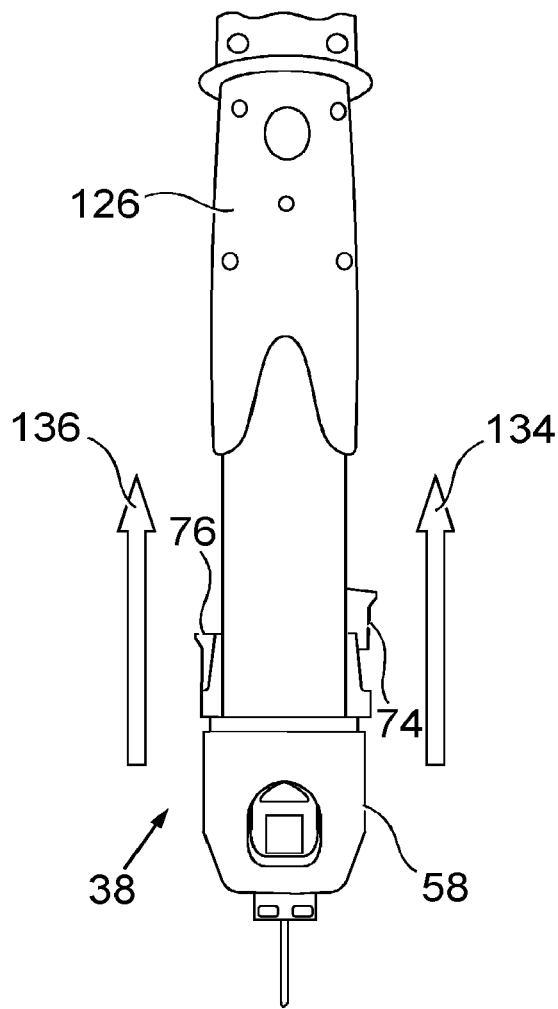
FIG. 11 is a side view of the handle of the delivery apparatus during a fourth stage of a method of deployment of a ring stent according to the invention.
Figure 13:
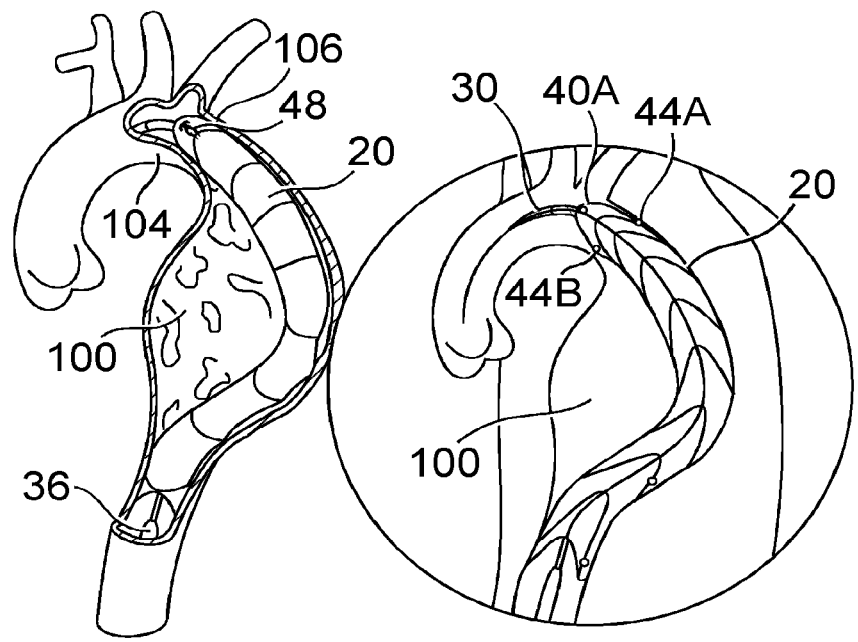
FIG. 13 is a schematic illustration of a thoracic arch during the fourth and fifth stages of a method of deployment of a ring stent according to the invention.

The position of the proximal ring stent 22 can now be adjusted to ensure that the ring stent 22 is positioned perpendicular to the lumen 100. The positions of the ring stent valleys 44, 46 are optimised by opening the valleys so that they are positioned perpendicular to the lumen wall 104, 106. The first ring stent valley 44 can be opened and collapsed by moving the corresponding first valley controller slider 74 forwards in the direction of arrow 134, as shown in FIG. 11, and backwards respectively. Similarly the second ring stent valley 46 can be opened and collapsed by moving the corresponding second valley controller slider 76 forwards in the direction of arrow 136, as shown in FIG. 11, and backwards respectively.

Figure 15:
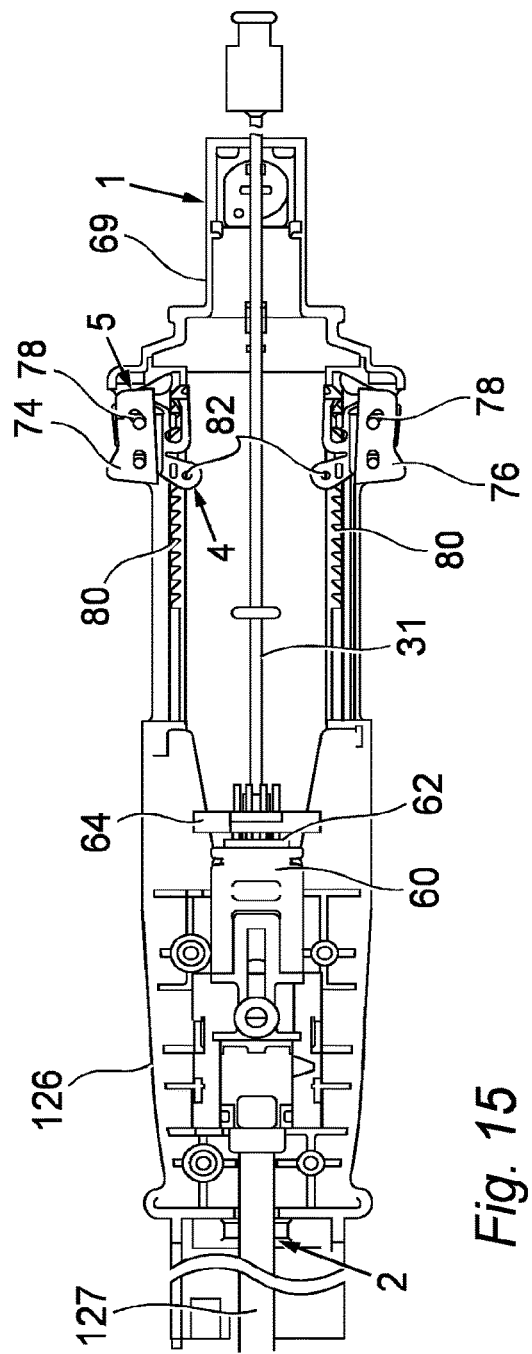
FIG. 15 is a partial sectional view through the control handle of the delivery apparatus of FIG. 1.
Figure 16:
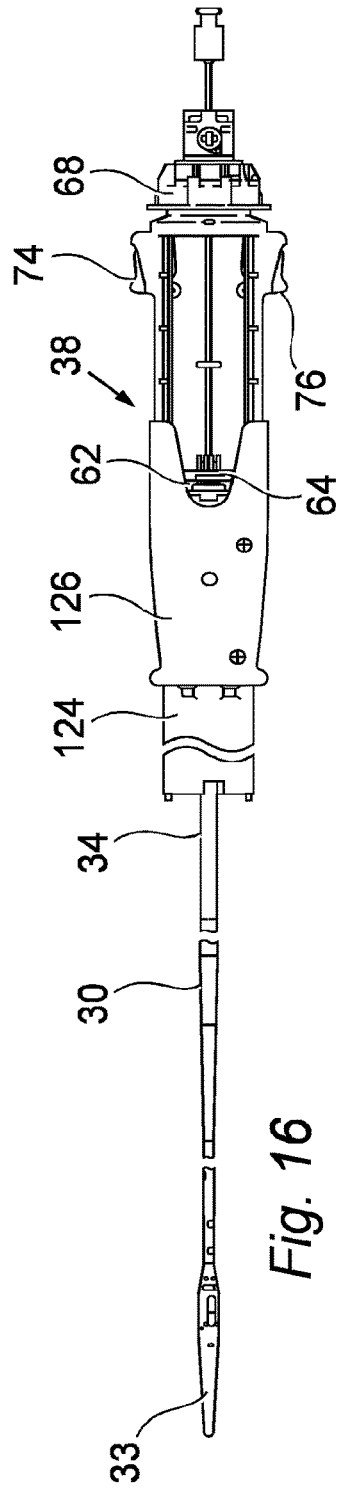
FIGS. 16 and 17 are a partial top view and a partial side view respectively of the delivery apparatus of FIG. 1.
Figure 17:
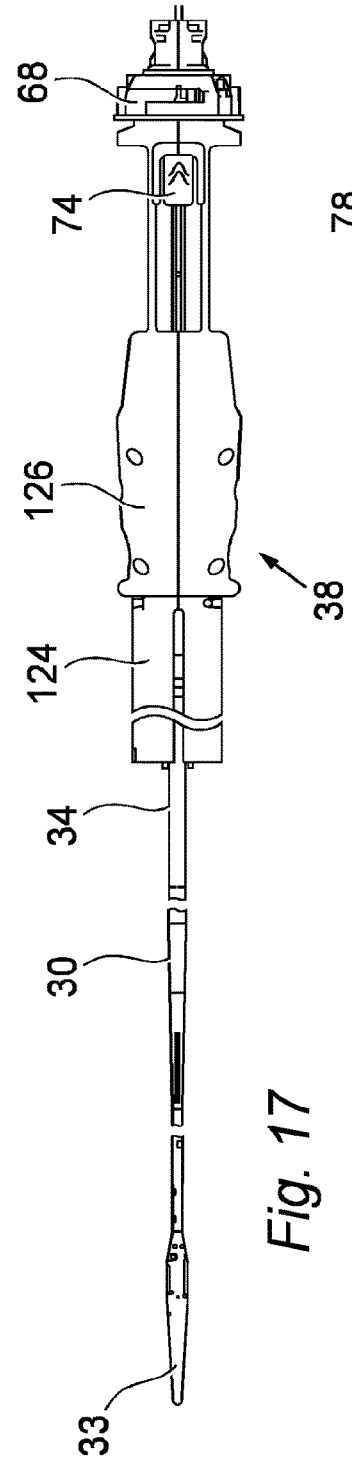
Figure 18:
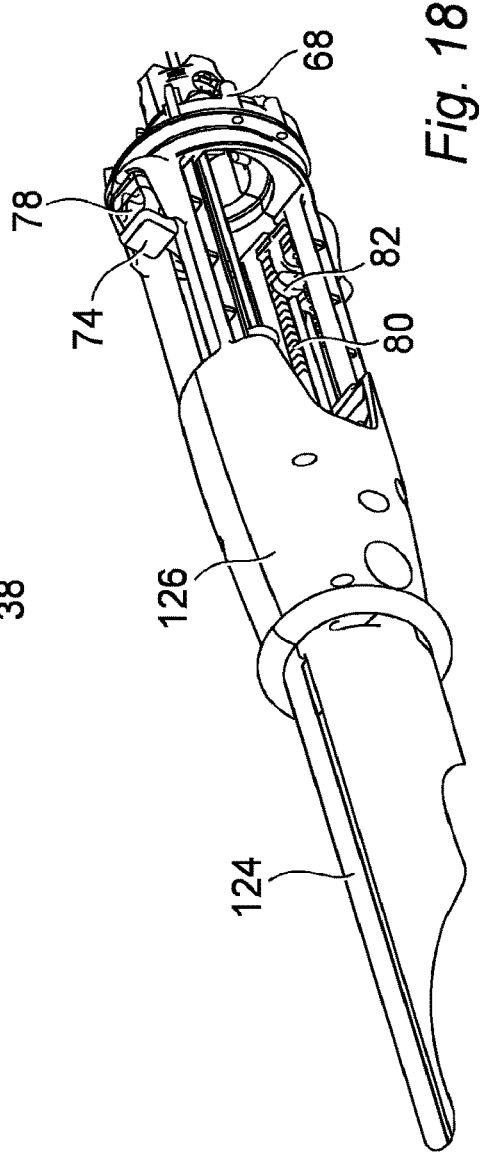
FIG. 18 is a partial isometric view of the control handle of the delivery apparatus of FIG. 1.
Figure 21:
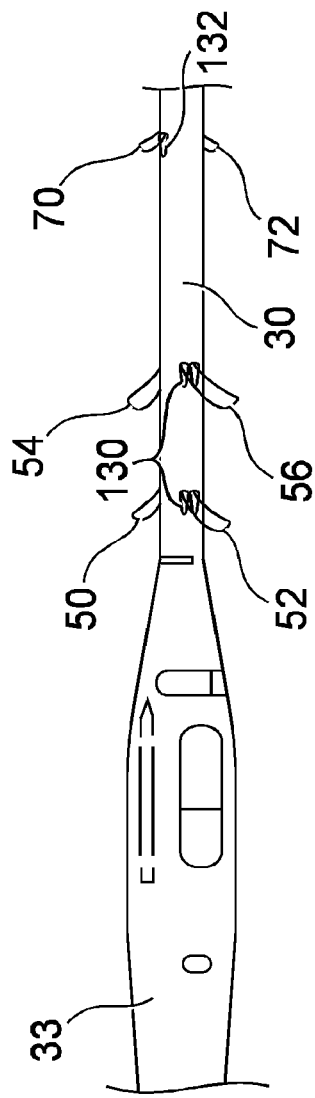
FIG. 21 is a schematic partial view of the proximal end of the delivery shaft of the delivery apparatus of FIG. 1 with the control wires installed.
Figure 22:
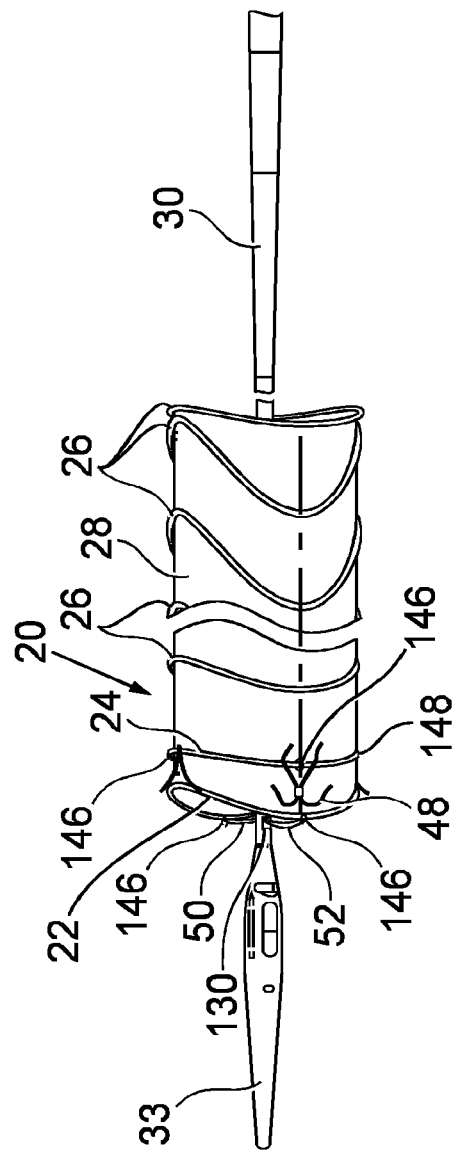
FIG. 22 is a schematic view of the stent graft on the delivery shaft of the delivery apparatus of FIG. 1 with the control wires installed.

Movement of the sliders 74, 76 results in movement of the corresponding stent valley control wires 70, 72 which extend from the control handle 38 along longitudinal passages 90 in the delivery shaft 30 and out of the delivery shaft 30 through apertures 132 to connection points 148 on the first and second ring stent valleys 44, 46 respectively. Each valley 44, 46 can be opened and closed independently of the other by moving the corresponding slider 74, 76. The resilience of the ring stent 22 urges the valleys 44, 46 towards the open position, but the sliders 74, 76 are provided with a ratchet 80, seen in FIGS. 15 and 18, so that they can only be moved when the operator releases the slider 74, 76 from the ratchet 80 by pressing on the actuator surface 78 of the slider 74, 76.

Figure 12:
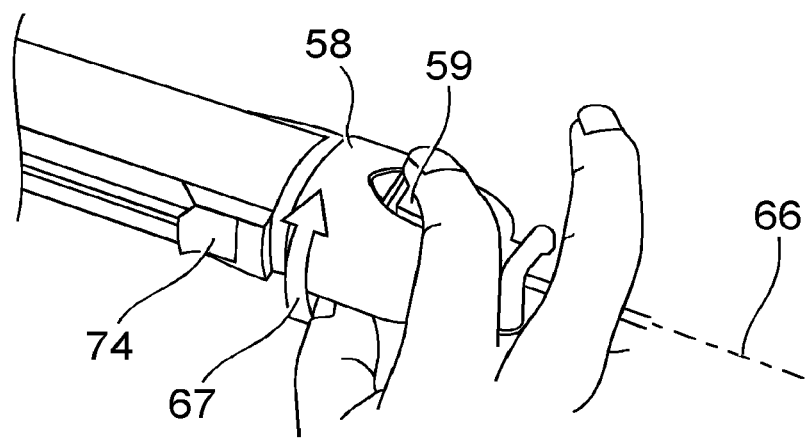
FIG. 12 is a view of the handle of the delivery apparatus during a fifth stage of a method of deployment of a ring stent according to the invention.

Once the valley positions are optimised, the peaks 40, 42 of the ring stent 22 can be opened so that the proximal portion of the stent graft 20 is engaged with the vessel wall 104, 106. The peaks 40, 42 are opened by depressing one or more buttons or tabs 59 on the peak controller rotary collar 58 and turning it in a clockwise direction in the direction of arrow 67 about the longitudinal axis 66 of the control handle, as shown in FIG. 12. Rotation of the collar 58 results in rotation of a peak controller winder 68 which permits movement of corresponding stent peak control wires 50, 52 which extend from the control handle 38 along longitudinal passages 90 in the delivery shaft 30 and out of the delivery shaft 30 through apertures 130 to connection points 146 on the first and second ring stent peaks 40A, 42A respectively, to permit the peaks to move way from the delivery shaft 30 under the resilience of the ring stent 22. Instead of only the peaks 40A, 42A of the first ring stent 22 being controllable, the peaks 40B, 42B of the second ring stent 24 or other ring stents 26 may also be connected by associated stent peak control wires 54, 56 coupled in the same way to the peak control winder 68, so that on rotation of the collar 58, the peaks 40B, 42B of the second ring stent 24 also move way from the delivery shaft 30 under the resilience of the ring stent 22.

The resilience of the ring stents 22, 24 urges the peaks 40, 42 towards the open position, but the button 59 prevents rotation of the collar 58 unless the button 59 is depressed, by means of a ratchet (not shown) so that the peaks 40, 42 can only be moved when the operator depresses the button 59.

Figure 14:
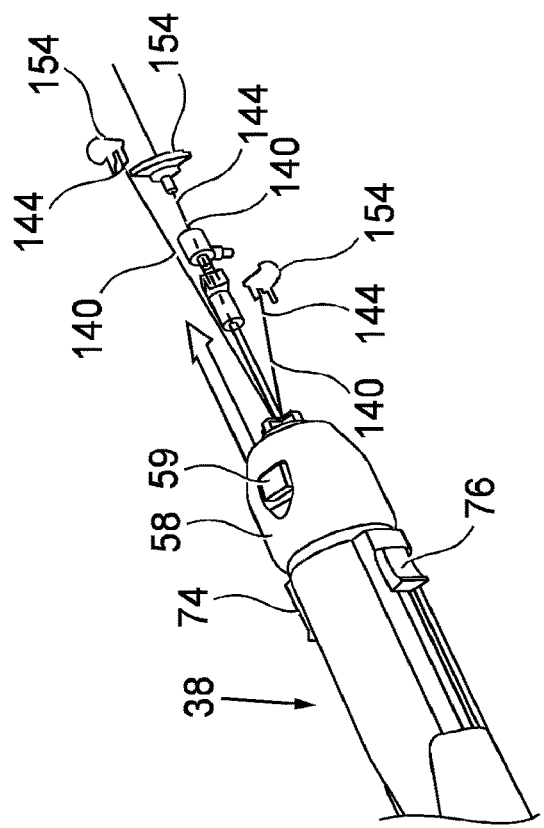
FIG. 14 is a view of the handle of the delivery apparatus during a sixth stage of a method of deployment of a ring stent according to the invention.

Once the peaks 40, 42 are fully opened the position of the ring stent 22 and stent graft 20 can be checked. If the position needs further adjustment, the peaks 40, 42 are retracted again to the collapsed position on the delivery shaft 30 by rotating the peak controller 58 in an anti-clockwise direction opposite to that of arrow 67, and then the valleys 44, 46 are similarly retracted by moving the sliders in the direction opposite to that of arrows 134, 136. The valleys and peaks can then be realigned to achieve a more accurate position. As before, once the valley positions are satisfactory, the peaks are opened to allow the stent graft 20 to engage with the vessel walls 104, 106 by means of the hooks 48. The release wires 140, whose proximal ends 96 hold the proximal end 92 of the stent graft 20 on the delivery shaft 30, and the looped back tether wires 98, which hold the distal end 94 of the stent graft 20 on the delivery shaft 30, can then be removed, prior to re-sheathing with the retractable sleeve 36 and removal of the delivery apparatus from the lumen 100. The proximal end 96 of each release wire 140 is associated with a connection 146, 148 between the stent graft 20 and one of the stent peak control wires 50, 52, the stent valley control wires 70, 72, and the tow or back tether wires 98, so that pulling the release wire 140 causes the connection 146, 148 to be broken. Such release wires 140 are known, for example in EP-A-910309, and are not described further. In the described embodiment the release wires travel through the proximal end 33 of delivery shaft 30 to assist in providing stability during the removal of the release wires. The distal ends 144 of the release wires 140 may each be secured to a release clip 154 mounted at the distal end of the control handle 38. The release wires 140 associated with the stent peak control wires 50, 52 and the stent valley control wires 70, 72 are also removed by pulling the corresponding release clip 154 distally along the longitudinal axis 66 of the control handle, as shown in FIG. 14.

The interior of the control handle is shown more clearly in FIGS. 15 to 18 with the handle access cover removed and with the control wires omitted for clarity. The control wires 50, 52, 54, 56, 70, 72 pass from the proximal end 33 of the delivery shaft 30 through one or more longitudinal passages in the delivery shaft 30 to the distal end 34 where they enter the shaft 124 of the control handle 38 through a central passage 127. The control wires 50, 52, 54, 56, 70, 72 then pass through a manifold 60 having a discrete tube aperture 62 for each control wire. This provides a smooth and continuous passage for each control wire from the connection point 146, 148 at the stent graft 20 to the peak controller 58 or valley controllers 74, 76. The manifold 60 enables feeder wires (not shown) to pass freely for loading the control wires when assembling the apparatus. Integral haemostasis valves are provided in a haemostasis switching plate 64 adjacent to the manifold 60 to allow flushing of the system with saline prior to use. The haemostasis valves also provide a controlled restriction to prevent excessive blood loss while maintaining control of the stent graft 20 by the apparatus. The manifold apertures may comprise passages which diverge from the connection with central passage 127 to the distal side of the haemostasis switching plate 64, to enable the control wires to be distributed and loaded onto the peak controller 58 or valley controllers 74, 76.

The valley controllers 74, 76 each include an actuating surface 78 which must be depressed to disengage the slider 74, 76 from the ratchet 80 to allow the slider to be moved. Once pressure is removed from the actuating surface 78, the slider 74, 76 becomes engaged again with the ratchet 80 and further movement of the slider 74, 76 is prevented. The valley controllers 74, 76 each include a connector 82 to which the corresponding stent valley control wire 70, 72 is connected.

The peak controller 58 includes a winder 68 (omitted in FIG. 15 but shown in FIGS. 16 to 20) which is mounted for rotation on a winder spindle 69. The rotary collar 58 is omitted for clarity in FIGS. 15 to 20. A ratchet plate (not shown) is mounted on the winder spindle 69 and provides bearing and ratchet interfaces to the winder 68.

The connection of the control wires 50, 52, 54, 56, 70, 72 is shown in FIGS. 19 to 22. Each wire may comprise a looped wire, having two strands, but is referred to in this specification as a single wire. At the distal end the stent valley control wires 70, 72 pass out of the manifold apertures 62 in the control handle 38 and are connected to the slider wire connectors 82. At the proximal end the stent valley control wires 70, 72 pass out of the valley apertures 132 in the delivery shaft 38 and are connected to the connection points 148 on the ring stent valleys 44, 46. In the illustrated example of FIG. 22 the stent valley control wires 70, 72 are connected to the connection points 148 on the valleys 44B, 46B on the second ring stent 24, but they could instead be connected to the valleys 44A, 46A on the first or third ring stent 22, 24, or to the valleys of two ring stents 22, 24, 26, or to the sleeve 28 between the ring stents 22, 24, 26.

At the distal end the stent peak control wires 50, 52, 54, 56 pass out of the manifold apertures 62 in the control handle 38, pass through apertures 160 and are connected to connection points on the peak controller winder 68. In the illustrated example the connection points are anchor pins or fixing clamps 162 which enable adjustment of the control wires to achieve the correct length. At the proximal end the stent peak control wires 50, 52, 54, 56 pass out of the peak apertures 130 in the delivery shaft 38 and are connected to the connection points 146 on the ring stent peaks 40A, 42A, 40B, 42B. In the illustrated example the stent peak control wires are connected to the connection points 146 on the peaks of the both the first and second ring stents 22, 24, but they could instead be connected to the peaks on the first ring stent 22 only, or the peaks of the second ring stent 24 only.

The apparatus and method of the invention allow the controlled rotation and orientation of a ring stent 22, 24 in a lumen 100 by selectively operating one of the first and second valley controllers 74, 76 to permit movement of the stent valley control wires 70, 72 along the delivery shaft 30 such that the first or second diametrically opposed valley connection point 148 on the ring stent 22, 24 is urged by the resilience of the ring stent to move away from the delivery shaft 30, thereby rotating the ring stent. The movement is reversible so that the valley connection point 148 can also be moved towards the delivery shaft 30 to a folded or contracted position. During assembly of the apparatus the stent graft 20 adopts its expanded position shown in FIG. 22, but prior to sheathing the two stent valley control wires 70, 72 are tensioned such that the valley connection points 148 are held by the stent valley control wires 70, 72 in a folded arrangement towards the delivery shaft. In addition the two stent peak control wires 50, 52, 54, 56 are tensioned such that the peak connection points 146 are also held in a folded arrangement towards the delivery shaft.

The apparatus and method of the invention allow the controlled deployment of a ring stent 22, 24 in a lumen 100 by operating the peak controller 58 to permit movement of the stent peak control wires 50, 52, 54, 56 along the delivery shaft such that the peak connection points 146 on one or more proximal ring stents 22, 24 are urged by the resilience of the ring stent to move away from the delivery shaft and the ring stent adopts a fully deployed position. The movement is reversible so that the peak connection point 146 can also be moved towards the delivery shaft 30 to a folded or contracted position if the ring stent requires repositioning.

The peak and valley connection points 146, 148 may be eyelets through which the looped control wires are threaded.

All documents referred to in this specification are herein incorporated by reference. Various modifications and variations to the described embodiments of the inventions will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the art are intended to be covered by the present invention.

We claim:

1. A delivery apparatus, the apparatus comprising:
   a delivery shaft with a tubular prosthesis mounted on a proximal end thereof for insertion into a lumen and a distal end remote from the proximal end, the tubular prosthesis comprising a sleeve and at least one discrete axially-extending ring stent that includes a plurality of peaks defining a first axial end thereof and a plurality of valleys defining a second axial end thereof opposite the first axial end, the plurality of peaks and the plurality of valleys being alternatingly arranged and comprising portions thereof that change axial directions, wherein the at least one discrete axially-extending ring stent is attached to the sleeve and configured to maintain patency of the sleeve after deployment of the tubular prosthesis;
   a retractable sleeve adapted to contain the tubular prosthesis mounted on the delivery shaft;
   a control handle proximate to the distal end of the delivery shaft;
   at least one stent peak control wire extending from the control handle and physically coupled to at least one peak of the plurality of peaks at an at least one peak connection point located directly at the at least one peak;
   at least one peak controller at the control handle adapted to control the position of the at least one stent peak control wire to selectively open the at least one peak from a collapsed state and collapse the at least one peak from an open state;
   at least one stent valley control wire extending from the control handle and physically coupled to at least one valley of the plurality of valleys at an at least one valley connection point located directly at the at least one valley; and
   at least one valley controller at the control handle adapted to control the position of the at least one stent valley control wire to selectively open the at least one valley from a collapsed state and collapse the at least one valley from an open state.

2. The apparatus of claim 1, wherein the at least one discrete axially-extending ring stent comprises a plurality of discrete axially-extending ring stents attached to the sleeve at spaced intervals.

3. The apparatus of claim 2, wherein the sleeve is a flexible tubular conduit.

4. The apparatus of claim 1, wherein the selectively opening and collapsing the at least one peak comprises selectively opening and collapsing at least a first portion of the at least one discrete axially-extending ring stent, and the selectively opening and collapsing the at least one valley comprises selectively opening and collapsing at least a second portion of the at least one discrete axially-extending ring stent.

5. The apparatus of claim 1, wherein the at least one discrete axially-extending ring stent of the tubular prosthesis is mounted on the delivery shaft in a collapsed configuration and is naturally biased into an open configuration from the collapsed configuration.

6. The apparatus of claim 1, wherein the at least one stent peak control wire is directly physically coupled to the at least one peak at the at least one peak connection point.

7. The apparatus of claim 1, wherein the at least one stent valley control wire is directly physically coupled to the at least one valley at the at least one valley connection point.

8. The apparatus of claim 1, wherein the at least one peak connection point comprises a respective peak connection loop.

9. The apparatus of claim 1, wherein the at least one valley connection point comprises a respective valley connection loop.

10. The apparatus of claim 1, wherein the at least one peak connection point comprises at least one peak eyelet, and the at least one stent peak control wire is threaded through the at least one peak eyelet.

11. The apparatus of claim 10, wherein the at least one stent peak control wire comprises at least one looped wire which extends from the control handle, to the at least one peak connection point, and back to the control handle.

12. The apparatus of claim 11, further comprising at least one release wire extending from the control handle and to the at least one peak connection point, and wherein release of the at least one release wire releases the at least one peak connection point such that the at least one stent peak control wire is physically decoupled from the at least one peak.

13. The apparatus of claim 1, wherein the at least one release wire is releasably coupled to the control handle.

14. The apparatus of claim 1, wherein the at least one valley connection point comprises at least one valley eyelet, and the at least one stent valley control wire is threaded through the at least one valley eyelet.

15. The apparatus of claim 14, wherein the at least one stent valley control wire comprises at least one looped wire which extends from the control handle, to the at least one valley connection point, and back to the control handle.

16. The apparatus of claim 15, further comprising at least one release wire extending from the control handle and to the at least one valley connection point, and wherein release of the at least one release wire releases the at least one valley connection point such that the at least one stent valley control wire is physically decoupled from the at least one valley.

17. The apparatus of claim 16, wherein the at least one release wire is releasably coupled to the control handle.

18. The apparatus of claim 1, wherein at least one of:
   the at least one peak connection point comprises at least one point on the at least one peak of the at least one discrete axially-extending ring stent; and
   the at least one valley connection point comprises at least one point on the at least one valley of the at least one discrete axially-extending ring stent.

19. The apparatus of claim 1, wherein the at least one discrete axially-extending ring stent comprises at least one discrete saddle-shaped ring stent, wherein the plurality of peaks are only a pair of peaks and the plurality of valleys are only a pair of valleys.

20. The apparatus of claim 19, wherein the pair of peaks are diametrically opposed to each other, and the pair of valleys are diametrically opposed to each other.

21. The apparatus of claim 1, wherein the at least one discrete axially-extending ring stent is formed of a resilient alloy material.

22. The apparatus of claim 1, wherein the at least one stent peak control wire comprises at least two stent peak control wires extending from the control handle, and wherein the at least one peak controller is adapted to control the position of the at least two stent peak control wires.

23. The apparatus of claim 1, wherein the at least one stent valley control wire comprises at least two stent valley control wires extending from the control handle, and wherein the at least one valley controller is adapted to control the position of the at least two stent valley control wires.

24. The apparatus of claim 1, wherein the delivery shaft includes a plurality of longitudinal passages, each stent peak control wire and stent valley control wire extending through a respective longitudinal passage.

25. The apparatus of claim 1, comprising one or more tow wires extending from the proximal end of the delivery shaft to a proximal end of the tubular prosthesis mounted on the delivery shaft.

26. The apparatus of claim 1, comprising one or more back tether wires extending from the proximal end of the delivery shaft to a distal end of the tubular prosthesis mounted on the delivery shaft.

27. The apparatus of claim 1, wherein the control handle includes a manifold having a plurality of apertures, each stent peak control wire and stent valley control wire extending through a respective aperture.

28. The apparatus of claim 27, wherein the manifold includes a plurality of haemostasis valves switchable between open and closed positions.

29. The apparatus of claim 1, wherein the at least one peak controller comprises a rotatable collar that is rotatable about a longitudinal axis of the control handle.

30. The apparatus of claim 29, wherein rotation of the rotatable collar about the longitudinal axis of the control handle selectively opens or closes at least a portion of the at least one discrete axially-extending ring stent.

31. The apparatus of claim 1, wherein the at least one valley controller comprises at least one slider.

32. The apparatus of claim 31, wherein the at least one valley controller includes at least one actuating surface and at least one ratchet adapted to allow the at least one slider to move when the at least one actuating surface is depressed and to hold the at least one slider in an engaged position when the at least one actuating surface is released.

33. The apparatus of claim 31, wherein the at least one slider is mounted for longitudinal sliding movement.

34. The apparatus of claim 31, wherein the at least one slider includes a wire connector to which is connected the at least one stent valley control wire.

35. The apparatus of claim 31, wherein sliding movement of the at least one slider in a first direction opens at least a portion of the at least one discrete axially-extending ring stent, and sliding movement of the at least one slider in a second direction collapses at least a portion of the at least one discrete axially-extending ring stent.

36. The apparatus of claim 1, wherein the at least one peak controller is positioned proximally relative to the at least one valley controller at the control handle.

37. The apparatus of claim 1, wherein the at least one peak controller and the at least one valley controller are separately controllable with respect to each other.

38. The apparatus of claim 1, wherein the at least one stent peak control wire comprises a first stent peak control wire and a second stent peak control wire, and the at least one stent valley control wire comprises a first stent valley control wire and a second stent valley control wire, wherein the at least one peak connection point comprises a first peak connection point and a second peak connection point, and the at least one valley connection point comprises a first valley connection point and a second valley connection point, wherein the plurality of peaks comprise a first peak and a second peak, and the plurality of valleys comprise a first valley and a second valley, wherein the first stent peak control wire is physically coupled to the first peak at the first peak connection point, and the second stent peak control wire is physically coupled to the second peak at the second peak connection point, and wherein the first stent valley control wire is physically coupled to the first valley at the first valley connection point, and the second stent valley control wire is physically coupled to the second valley at the second valley connection point.

39. The apparatus of claim 38, wherein the at least one valley controller comprises a first valley controller and a second valley controller, and wherein the first valley controller is adapted to control the position of at least the first stent valley control wire to selectively open at least the first valley from the collapsed state and collapse at least the first valley from the open state, and the second valley controller is adapted to control the position of at least the second stent valley control wire to selectively open at least the second valley from a collapsed state and collapse at least the second valley from an open state.

40. A method, comprising:
providing the delivery apparatus of claim 1;
holding the at least one stent peak control wire under tension such that the at least one peak connection point is held by the at least one stent peak control wire and the at least one peak is held in a collapsed arrangement positioned proximate to the delivery shaft;
holding the at least one stent valley control wire under tension such that the at least one valley connection point is held by the at least one stent valley control wire and the at least one valley is held in a collapsed arrangement positioned proximate to the delivery shaft;
operating the at least one peak controller and the at least one valley controller to permit movement of the at least one stent peak control wire and the at least one stent valley control wire along the delivery shaft such that the at least one peak and the at least one valley are urged by resilience of the at least one discrete axially-extending ring stent to adopt at least partially deployed positions positioned distal to the delivery shaft as compared to the collapsed arrangement.

41. The method of claim 40, further comprising further operating the at least one peak controller and the at least one valley controller to effectuate movement of the at least one stent peak control wire and the at least one stent valley control wire along the delivery shaft such that the at least one peak and the at least one valley are forced toward the delivery shaft to at least partially collapsed arrangements.

42. The method of claim 40, wherein operating the at least one peak controller and the at least one valley controller comprises separately operating the at least one peak controller and the at least one valley controller with respect to each other.

43. The method of claim 40, wherein the at least one peak controller is positioned proximally relative to the at least one valley controller at the control handle.

44. The method of claim 40, wherein operating the at least one peak controller and the at least one valley controller comprises rotating and axially sliding the at least one peak controller and the at least one valley controller, respectively.

45. The method of claim 40, wherein at least one of:
the at least one stent peak control wire is directly physically coupled to the at least one peak at the at least one peak connection point; and
the at least one stent valley control wire is directly physically coupled to the at least one valley at the at least one valley connection point.

46. The method of claim 40, wherein the at least one peak connection point comprises at least one peak eyelet, and the at least one stent peak control wire is threaded through the at least one peak eyelet, and wherein the at least one stent peak control wire comprises at least one looped wire.

47. The method of claim 46, wherein the delivery apparatus further comprises at least one release wire extending from the control handle and to the at least one peak connection point, and wherein the method further comprises releasing the at least one release wire to release the at least one peak connection point to physically decouple the at least one stent peak control wire from the at least one peak.

48. The method of claim 40, wherein the at least one valley connection point comprises at least one valley eyelet, and the at least one stent valley control wire is threaded through the at least one valley eyelet, and wherein the at least one stent valley control wire comprises at least one looped wire.

49. The method of claim 48, wherein the delivery apparatus further comprises at least one release wire extending from the control handle and to the at least one valley connection point, and wherein the method further comprises releasing the at least one release wire to release the at least one valley connection point to physically decouple the at least one stent valley control wire from the at least one valley.

* * * * *

UNITED STATES PATENT AND TRADEMARK OFFICE
CERTIFICATE OF CORRECTION

Page 1 of 1

PATENT NO. : 11,026,823 B2
APPLICATION NO. : 16/180804
DATED : June 8, 2021
INVENTOR(S) : McDonald et al.

It is certified that error appears in the above-identified patent and that said Letters Patent is hereby corrected as shown below:

In the Claims

Column 14, Line 37: Claim 13, Delete "claim 1" and insert -- claim 12 --

Signed and Sealed this
Twentieth Day of July, 2021

Drew Hirshfeld
*Performing the Functions and Duties of the
Under Secretary of Commerce for Intellectual Property and
Director of the United States Patent and Trademark Office*